United States Patent [19]

Magdelaine et al.

[11] Patent Number: 5,455,639
[45] Date of Patent: Oct. 3, 1995

[54] PROTECTIVE EYEWEAR WITH REPLACEABLE LENS

[75] Inventors: Guy Magdelaine, Vaux les Saint Claude; Bernard Reymondet, Saint Claude, both of France

[73] Assignee: WGM Safety Corp., Reading, Pa.

[21] Appl. No.: 144,953

[22] Filed: Oct. 29, 1993

[51] Int. Cl.$^6$ .............................. G02C 1/00; G02C 5/00; G02C 7/10
[52] U.S. Cl. .................. 351/47; 351/44; 351/85; 351/86; 351/106; 351/111; 2/448
[58] Field of Search .................. 2/12, 15, 425, 2/429, 430, 439, 448; 351/41, 44, 47, 52, 84, 85, 86, 91, 92, 96, 106, 111, 122, 144, 178, 158

[56] References Cited

U.S. PATENT DOCUMENTS

| | | | |
|---|---|---|---|
| D. 337,595 | 7/1993 | Reymondet et al. | D16/112 |
| 1,805,396 | 5/1931 | Havens . | |
| 1,879,216 | 9/1932 | Nnan et al. . | |
| 2,176,006 | 10/1939 | Ehrlich | 2/13 |
| 2,177,610 | 10/1939 | Ehrlich | 2/12 |
| 2,281,129 | 4/1942 | Wolff | 351/44 |
| 2,423,539 | 7/1947 | Williams | 88/41 |
| 2,574,839 | 11/1951 | Pelzer | 88/47 |
| 2,582,345 | 1/1952 | Moeller | 88/55 |
| 2,607,919 | 8/1952 | Stegeman | 2/14 |
| 2,663,021 | 12/1953 | Douglass | 2/14 |
| 2,700,765 | 2/1955 | Hoffmaster | 2/14 |
| 2,756,631 | 7/1956 | Page | 88/47 |
| 2,824,309 | 2/1958 | Fleming | 2/14 |
| 3,155,982 | 11/1964 | Baratelli | 2/12 |
| 3,229,303 | 1/1966 | Jonassen | 2/14 |
| 3,233,250 | 2/1966 | Jonassen | 2/14 |
| 3,261,652 | 7/1966 | Magnus | 351/118 |
| 3,384,903 | 5/1968 | Malcom, Jr. | 2/14 |
| 3,389,406 | 6/1968 | Mitchell | 2/14 |
| 3,434,780 | 3/1969 | Bolden | 351/41 |
| 3,471,222 | 10/1969 | Eisler | 351/61 |
| 3,475,083 | 10/1969 | Gitlin et al. | 351/41 |
| 3,497,294 | 2/1970 | Volk | 351/41 |
| 3,577,566 | 5/1971 | Kislin et al. | 2/12 |
| 3,604,013 | 9/1971 | Hammond | 2/13 |
| 3,614,216 | 10/1971 | Rosenthal | 351/44 |
| 3,674,344 | 7/1972 | Lacy | 350/312 |
| 3,689,139 | 9/1972 | Gross et al. | 353/84 |
| 3,782,810 | 1/1974 | Marker | 351/47 |
| 3,838,914 | 10/1974 | Fernadez | 351/106 |
| 4,470,673 | 9/1984 | Gilson et al. | 351/44 |
| 4,515,448 | 5/1985 | Tackles | 351/41 |
| 4,542,964 | 9/1985 | Gilson et al. | 351/44 |

(List continued on next page.)

FOREIGN PATENT DOCUMENTS

| | | |
|---|---|---|
| 7122565 | 6/1971 | France . |
| 2617294 | 12/1988 | France . |
| 522927 | 10/1954 | Italy . |
| 511927 | 1/1955 | Italy . |
| WO91/17468 | 5/1991 | WIPO . |

*Primary Examiner*—Anita Pellman Gross
*Assistant Examiner*—David R. Parsons
*Attorney, Agent, or Firm*—Seidel, Gonda, Lavorgna & Monaco

[57] ABSTRACT

A protective eyewear including a brow member, two temple arm members, a front lens and two side shields. The front lens is removably attached to the brow member within a channel formed therein. The lens includes a series of projections adjacent one edge thereof and the brow member including a corresponding series of slots opening into the channel. The projections on the lens are engaged within the slots in the brow member to lock the lens within the brow channel. The side shields are attached to the corresponding temple arm members by means of at least one projecting hub which is engaged within the temple arm. The nub preferably includes a central opening. The temple arm is molded to the side shield such that the temple arm material fills the central opening and engages the hub to lock the side shield in position. The eyewear provides a removable lens and also forms a protective structure that meets the eyewear impact resistance standards.

19 Claims, 3 Drawing Sheets

U.S. PATENT DOCUMENTS

| | | | |
|---|---|---|---|
| 4,674,851 | 6/1987 | Jannard | 351/47 |
| 4,730,915 | 3/1988 | Jannard | 351/47 |
| 4,741,611 | 5/1988 | Burns | 351/44 |
| 4,815,838 | 3/1989 | Liautaud | 351/158 |
| 4,824,233 | 4/1989 | Jannard | 351/47 |
| 4,859,048 | 8/1989 | Jannuard | 351/159 |
| 4,877,320 | 10/1989 | Holden | 351/44 |
| 4,878,749 | 11/1989 | McGee | 351/52 |
| 4,934,807 | 6/1990 | Bollé et al. | 351/62 |
| 4,964,714 | 10/1990 | Weymouth, Jr. et al. | 351/62 |
| 4,976,530 | 12/1990 | Mackay et al. | 351/44 |
| 4,997,267 | 3/1991 | Morrison et al. | 351/41 |
| 5,018,223 | 5/1991 | Dawson et al. | 2/436 |
| 5,146,623 | 9/1992 | Paysan et al. | 2/12 |
| 5,208,614 | 5/1993 | Jannard | 351/41 |

PROTECTIVE EYEWEAR WITH REPLACEABLE LENS

FIELD OF THE INVENTION

The present invention relates to eyewear, such as glasses, sun glasses, sports glasses, and the like. In particular the eyewear of the present invention is intended to protect the eyes from flying objects in a work environment and the like. The present invention also relates to protective eyewear in which the front lens is replaceable.

BACKGROUND OF THE INVENTION

Protective eyewear are typically utilized in a work related environment in which flying objects or projectiles may be present. An example of such a work environment is carpentry in which the use of a power saw may cause wood splinters to spray away from the cutting area. In order to protect the eyes, a front lens assembly is usually worn, whether or not the user requires corrective lenses. Also, side shields are provided on or adjacent the temple arms of the eyewear to prevent objects from striking the eyes frown the side.

Weight is typically a deterrent to the wearing of the eyewear. Thus, it is preferred that the eyewear be lightweight and comfortable so as to encourage its use. Many protective eyewear that are presently available utilize plastic lenses and frame members and are lightweight. These eyewear also include the desired comfort elements of regular glasses.

Because of the use of plastic for the lens and/or the side shields for the eyewear, the materials tend to be abraded during normal use. Lightweight objects moving across the lens surface may cause scratches therein which affect the clarity of the lens. Additionally, placement of the lens in a pocket, tool chest or the like may cause further scratching. In this regard, it may be preferable that the lens be replaceable.

Another feature that may be applied to eyewear is the use of color shading on the lens. The lens may include an amber or yellow coloring for increased visibility, or other coatings as desired. In certain situations, a replaceable lens assembly may be appropriate so that different shadings can be used on the same pair of eyewear.

In order to be classified as protective eyewear, the eyewear must meet certain standards. These standards apply to impact resistance, burning rate and replacement of the lens. In addition, certain test methods are identified within these standards. The standards for Canada are set by the Canadian Standards Association (CSA) and are generally defined in CSA Z94.3-92. In the United States, the American National Standard Institute (ANSI) has set standards under the designation Z87.1-1989.

BRIEF SUMMARY OF THE INVENTION

The present invention generally defines eyewear having a frame formed by a brow member and opposite side temple arm members. A removable front lens is attached to the brow member in a manner that preferably meets the standards for protective eyewear. The eyewear may include side shields that accompany each temple arm. These side shields preferably engage the edge of the front lens so as to eliminate any gap therebetween.

The preferred engagement of the front lens with the brow member is formed by a series of slots in the brow member which are located at various positions across the rear of the eyewear. A corresponding series of projections are found on the lens. The brow member forms a channel in which the lens is inserted during assembly. Upon insertion of the lens, the projections move into the slots to lock the lens to the brow member.

The connection of the temple arms with the side shields is preferably created during molding of the temple arm. The side shield includes a series of nubs which project above the side shield preferably in the plain of the shield and which preferably have a central opening therein. The temple arms are molded over the nubs and fill the central opening therein so as to lock the arm to the side shield. In this manner, the side shield is permanently locked to the arm.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE DRAWINGS

Figure 1:
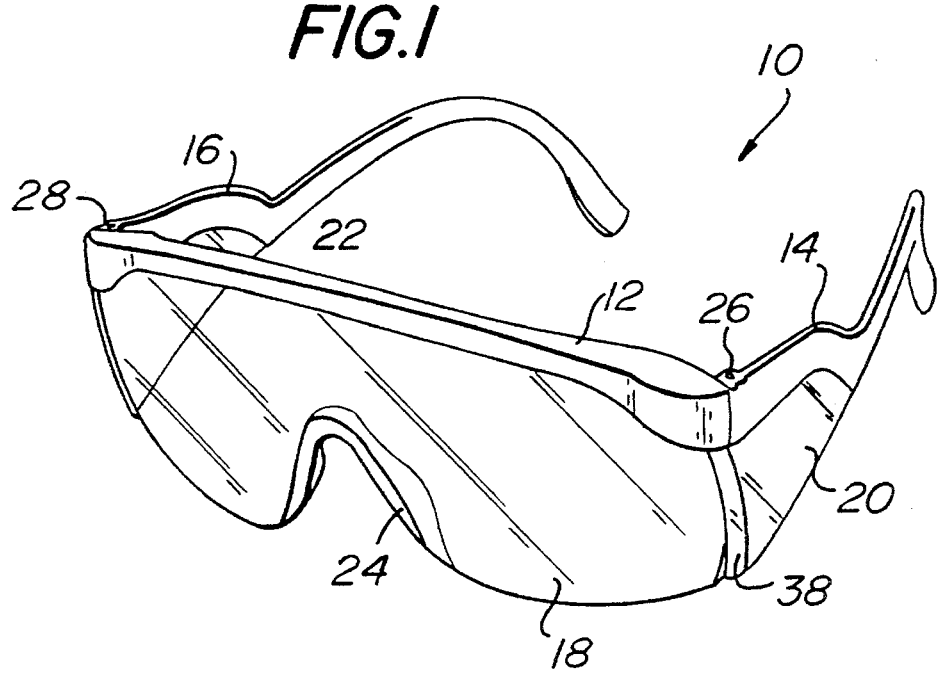
FIG. 1 is an isometric view of a protective eyewear in a form that includes the present invention.

In the figures, where like numerals indicate like elements, there is shown in FIG. 1 a preferred form of a protective eyewear which is generally designated by the numeral 10. The eyewear 10 may take a number of different forms as desired and the present invention is not limited to the specific form shown in the drawings.

The eyewear 10 generally includes a frame formed from a brow member 12 and opposite side temple arm members 14 and 16. Attached to the brow member 12 is a single front lens 18. Attached to the opposite side temple arm members 14 and 16 are side shields 20 and 22, respectively. The front lens 18 includes an integral nose bridge 24. Although the preferred embodiment of the nose bridge 24 is a molded portion of a single front lens 18, a separate detachable nose bridge which engages the front lens or multiple lenses may also be provided without departing from the present invention. The temple arms 14, 16 are attached to the brow member 12 on opposite sides thereof at hinges 26 and 28, respectively. The hinges 26, 28 may be formed in any manner as desired and as shown generally include interlocking tabs having a central pin.

The front lens 18 is preferably made of an optical quality, clear or colored, transparent or translucent polycarbonate material. The polycarbonate material is preferred because of the desired usage of the eyewear 10 for safety or protective purposes. However, other materials, such as acrylic or the like, may be used. The lens 18 may be coated with various organic coatings, in one layer or more, using dip, spray or other coating methods, to improve resistance to abrasion and scratching, reduce fogging and static charge, and improve cleanability of the lens. The lens may also be coated with non-organic materials, such as chrome, using vacuum evaporation or other processes. The side shields 20, 22 are also preferably made of a polycarbonate material. The front lens 18 preferably includes a slight curvature across the face of the wearer. (See FIG. 3.) The side shields 20, 22 may also have a curvature. (See FIG. 2.)

The brow member 12 is preferably made of a flexible plastic material so that it may be twisted away from the engagement with the front lens 18 for removal of the existing lens 18 and replacement with a separate lens. A discussion of the removal of the lens 18 from the brow member 12 is found below. Preferably, the brow member 12 and the temple arms 14, 16 are made of a nylon material. However, polyester materials are also possible.

The intent of the materials and assembly of eyewear 10 is to prevent cracking, fragmentation or breaking upon impact by a projectile. However, the eyewear having the features of the present invention may be included in other eyewear, such as sun or sport glasses or the like.

The overall construction of the eyewear 10 is intended to meet the ANSI and CSA impact resistance requirements. The ANSI standard for high velocity impact requires the frame and lens of the eyewear to resist impact of a ¼" diameter steel ball traveling at a velocity of 150 feet per second. In this test, the path of the projectile is adjusted so that it is directed at the center of either eye and a new set of eyewear is used for each impact position. The CSA standard for eye and face protection for high impact requires a similar test with the ball traveling at a velocity of 152 feet per second. The CSA projectile may be directed at any point on the eyewear. The point of impact for this test is randomly selected but is not placed at a position that would significantly increase failure due to the previous or nearby impacts. Failure of these tests would result from any parts or fragments being ejected from the eyewear that could contact the eye; lens fracture; lens and frame deformation or penetration; and/or frame fracture or separation from other parts.

Figure 3:
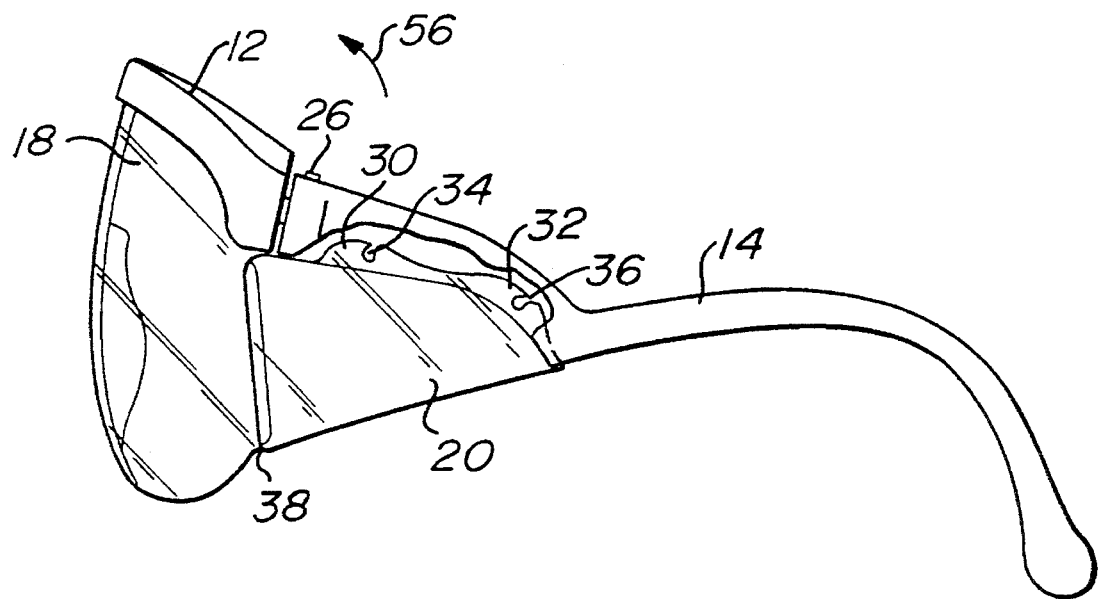
FIG. 3 is a side view of the eyewear showing the engagement of the side shield with the temple arm as part of its molding.

In FIG. 3 there is shown a preferred construction of the temple arm 14 and side shield 20. It is generally contemplated that the combination of the opposite side temple arm 16 and side shield 22 would be the same as that shown in this FIG. 3 but in mirror image.

The side shield 20 is formed separately from the temple arm 14. Preferably, the side shield includes nubs 30 and 32 each having a central opening 34 and 36, respectively. In the molding of the temple arm 14, the nubs 30, 32 and openings 34, 36 are positioned within the mold cavity adjacent the front portion of the temple arm 14 and hinge 26. The remaining portion of the side shield 20 projects outside of the mold. Upon filling the mold to form the temple arm 14, the nubs are covered. In addition, the molded material fills the central openings 34, 36. Upon solidification, the side shield 20 is locked into position by means of the nubs 30, 32 and the openings 34, 36. It is preferred that the side shield 14 be locked in position rather than be removable. It should be noted, however, that the nubs may take any form as desired. Such may include nubs which increase in cross-section as they project from the side shield. This would cause the material of the temple arm to flow around the nubs and lock the side shield.

Figure 2:
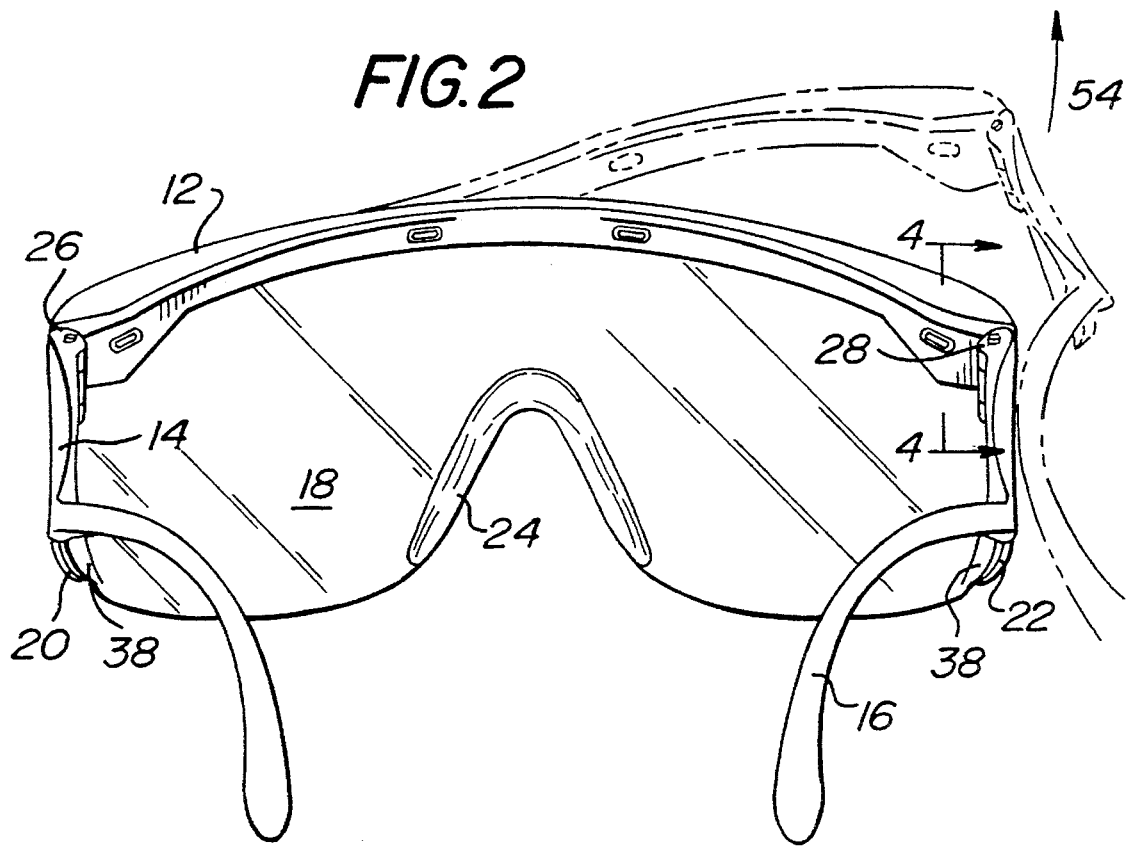
FIG. 2 is a rear view of the protective eyewear of FIG. 1 showing in phantom the flexing of a brow member for removal of the front lens therefrom.

As also can be seen in FIG. 3, the side shield 20 is supported on the temple arm 14 so that it overlaps with the front lens 18. The overlap is generally designated by the numeral 38 as is illustrated in FIGS. 1, 2 and 3. The overlap 38 is in part formed by a curvature of the side shield 20 in the area of the side edge of the lens 18. When the temple arm 14 is pivoted about the hinge 26, the side shield 20 also pivots. This pivoting action occurs without the side shield 20 interfering with the front lens 18, which would prevent the closure of the eyewear 10. When the side shield 20 and temple arm 14 are in their normal wearing position, the overlap 38 prevents projectiles and the like from moving between the front lens 18 and the side shield 20 towards the side of the face or eye.

Figure 4:
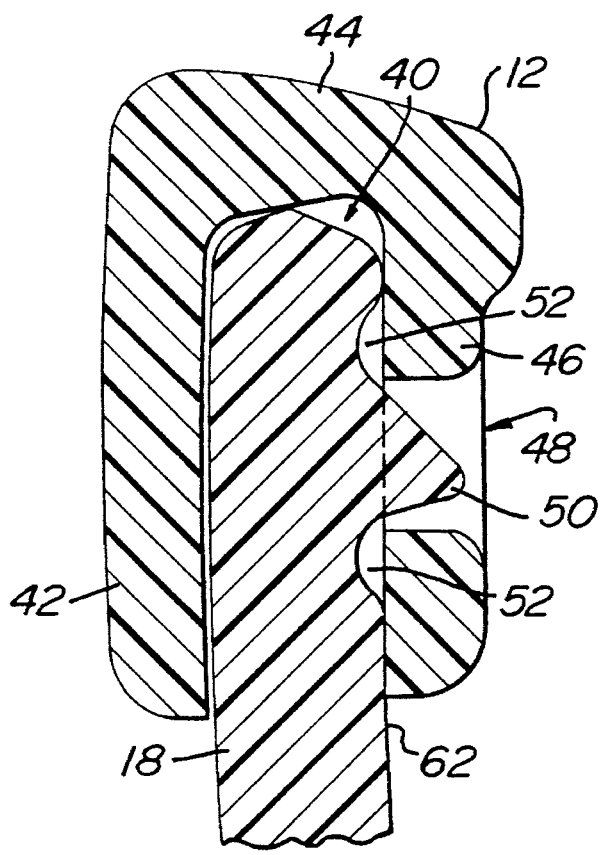
FIG. 4 is a cross-sectional view of the brow member showing its engagement with the front lens.
Figure 5:
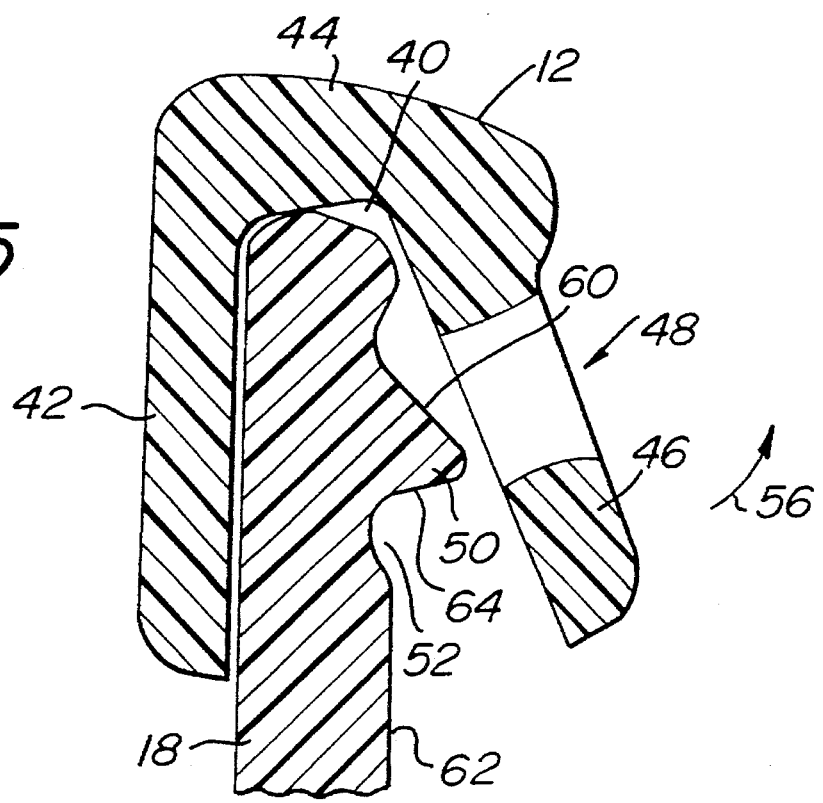
FIG. 5 is a second cross-sectional view of the brow member showing the preferred method of removal of the lens.

In FIGS. 4 and 5 there is shown cross-sections of the brow member 12 and the front lens 18 as taken through line 4—4 in FIG. 2. FIG. 4 illustrates the preferred form of engagement between the front lens 18 and the brow member 12 in securing the front lens to the frame. FIG. 5 illustrates the movement of the flexible brow member 12 during removal of the lens 18.

The brow member 12 generally forms a channel 40 having a front wall 42, a top wall 44 and a rear wall 46. Formed within the rear wall 46 is a series of slots 48 (shown in FIG. 2). A single slot is shown in FIGS. 4 and 5. The slot 48 includes walls which are substantially perpendicular to the formation of the rear wall 46 of channel 40. The lens 18 is inserted into the channel 40 with its top edge generally conforming to the dimensions of the channel 40. The front surface of the lens 18 is positioned flush with the front wall 42 of channel 40. The side edges of the lens 18 are preferably fit (not shown) into channel 40 with the lens having limited lateral movement.

The rear surface of the lens 18 includes a series of projections 50 which are engaged within the slots 48 in rear wall 46 of the brow 12. As illustrated in FIG. 4, each projection 50 generally includes a triangular cross-section having rounded surfaces thereon. The projecting edge of the triangle 50 is directed outwardly from the rear surface 62 of the lens 18. The base of the projection 50 is provided with a radiused groove 52. The groove 52 is preferably provided into the rear surface 62 of the lens 18 and surrounds the projection 50 on all sides. The top of the lens 18 generally engages the top wall 44 of channel 40, although as shown the surfaces are not required to be flush. All edges of the front lens 18 are preferably rounded or chamfered.

The formation of the radiused groove 52 and the rounded edges on the lens 18 are contemplated to prevent cracking of the lens. Angled surface may more easily cause a crack to occur or extend across the lens and cause a failure with respect to the designated standards. Moreover, the engagement of the projection 50 within slot 48 in the brow member 12 and the flush fit of the lens 18 within channel 40 fixes the lens 18 to the brow member 12 and prevents the lens 18 from separating during use.

The engagement of the lens 18 by the brow member 12 and the materials of the brow member 12 are preferably formed so that the lens 18 may be removed from the brow member 12 as shown in FIGS. 2 and 5. The flexibility of the brow member 12 with respect to the rigid lens 18 permits the disengagement of the projections 50 from slots 48 and the removal of the top of the lens 18 from channel 40.

As illustrated in FIG. 2, removal of the lens 18 is accomplished by the lifting of a temple arm, such as arm 16, in a direction shown by arrow 54. Simultaneously, the temple arm 16 should be pivoted forward. In FIG. 3, the direction of the pivot of the temple arm is shown by example with reference to temple arm 14. The pivoting of the arm, whether the right or left side of the brow is being removed, is generally shown by arrow 56. The effect of this pivoting movement 56 is shown in FIG. 5.

In FIG. 5, the rear wall 46 is shown as pivoted about the top wall 44 as a result of the lifting action (arrow 54 in FIG. 2) and the pivoting motion 56 (FIG. 5) of the arm 16. This pivoting movement 56 causes the rear wall 46 and its slot 48 to move away from the projection 50 on lens 18. Once the slot 48 on the brow 12 adjacent arm 16 moves away from the projection 50, the other projections on the lens 18 can be easily removed from their engagement position by a continued lifting of the brow member 12 as shown in FIG. 2 by arrow 54. It is the original twisting of the brow member 18, as shown in FIGS. 3 and 5, that creates the necessary release of the lens 18. This is due the formation of the triangular projections 50.

As illustrated, the top surface 60 of the projection 50 is formed at a relatively slight angle with respect to the rear surface 62 of the lens 18. This slight angle of surface 60 permits the lens 18 to be easily inserted into the channel 40 of the brow member 12 and create a lifting of the rear wall 46 prior to locking within slot 48. The bottom surface 64 of the projection 50 is formed at a relatively steep angle with respect to lens surface 62. This steep angle substantially prevents the lens 18 from being removed from the channel 40 by an upward force on the brow member—arrow 54, FIG. 2 (or a downward force applied to the lens 18). The bottom surface 64 of the projection 50 will not easily move the rear wall 46 to permit release from the slot 48. The twisting or pivoting motion 56 of rear wall 46 away from the projection 50 removes the slot 48 from its engagement with projection 50.

Figure 6:
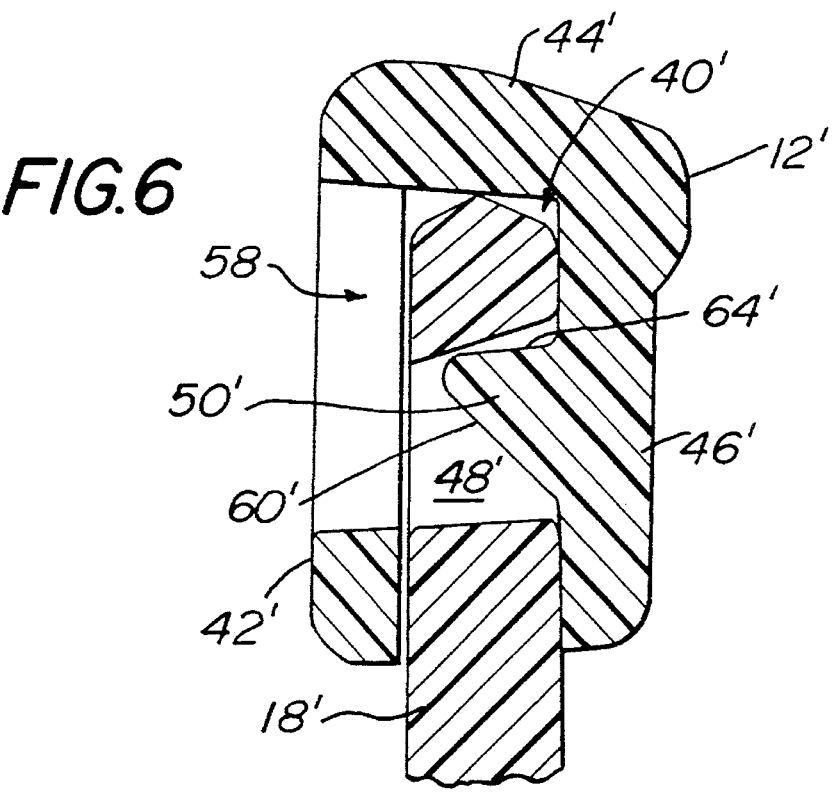
FIG. 6 is a second cross-sectional view of the brow member showing an alternate variation of the brow member and lens engagement.

An alternate construction of the engagement between the brow member and the lens is shown in FIG. 6. In this embodiment, the lens 18' generally includes a slot 48'. The rear wall 46' includes a projection 50' directed inwardly into the channel 40' and is formed to engage within the slot 48' within the lens 18'. The edges of the slot 48' are contemplated to be rounded. The triangular projection 50' is contemplated to be formed similar to projection 50 in FIG. 4 except that it is reversed. Surface 60' includes a slight angle and is formed on the bottom of the projection 50'. The steep angled surface 64' is provided on the top of the projection 50'. As should be understood by reference to FIG. 6 and the description above, this reversal of parts results from the location of the slot 48' in the lens 18' and the desire to resist movement of the lens 18' downwardly in the channel 40'. This engagement of the projection 50' and slot 40' fixes the lens 18' while also permitting removal in the manner contemplated by FIG. 5.

As can also be seen in FIG. 6, an opening 58 is provided in the front surface 42' of the brow member 12'. This opening 58 provides access to the channel 40' and projection 50' on the inside of rear wall 46'. The brow member 12' (and member 12) will preferably be formed by an injection molding process. Without the opening 58, the projection 50' likely could not be formed inside of the channel 40'. The opening 58 provides access to the mold parts and permits separation thereof. It is noted that the formation of an opening in the front surface of brow member 12' may not be desired for aesthetic reasons or otherwise. Other embodiments and variations thereof are also possible.

As can be seen in FIG. 2, a series of slots and projections are provided within the brow member 12 at various locations. This combination further enhances the fixing of the lens 18 within the channel 40 and 40' of the brow members 12 and 12' as shown in FIGS. 4–5.

The manner in which the lens is attached to the brow member as contemplated by the present invention gives the eyewear the strength to pass the protective eyewear tests such as those contained in the ANSI and CSA standards. While this attachment method is contemplated to be extremely strong, it is also designed to make lens changing easy to perform. Also, the openings in the brow member, where the projection inserts into the slot, make it easy for the wearer to see if the lens has been properly inserted into the frame.

The present invention may be embodied in other specific forms without departing from the spirit or essential attributes thereof, and accordingly, reference should be made to the appended claims, rather than to the foregoing specification, as indicating the scope of the invention.

We claim:

1. Eyewear comprising: a brow member; two temple arm members, each temple arm pivotally attached to opposite ends of the brow member; a lens removably attached to the brow member within a channel formed in the brow member; the lens having a generally curved plane portion and having a series of projections adjacent to one edge thereof, the projections protruding from and out of the plane of the plane portion; and the brow member having a corresponding series of slots opening into the channel, the projections on the lens engaged within the slots in the brow member to lock the lens within the channel.

2. Eyewear as claimed in claim 1 further comprising two side shield members, each one of said side shield members attached to one of the temple arm members.

3. Eyewear as claimed in claim 2 wherein the side shields each include a projecting nub which extends into and is encased within the temple arm, the temple arm to surround and encase the nub to lock the side shield in position.

4. Eyewear as claimed in claim 1 wherein the projections on the lens include a substantially triangular cross-section perpendicular to the plane portion, the triangular cross-section having a base integral with the plane portion and an apex for projecting into the openings in the channel.

5. Eyewear as claimed in claim 1 wherein a radiused groove having curved edges is formed in the lens, surrounding the projections.

6. Eyewear as claimed in claim 1 wherein the lens member is made of a polycarbonate material and the brow member and temple arm members are made of a flexible plastic material.

7. Eyewear comprising: a brow member; two temple arm members, each temple arm pivotally attached to opposite ends of the brow member; a lens removably attached to the brow member within a channel formed in the brow member; the lens having a series of projections adjacent to one edge thereof; the brow member having a corresponding series of slots opening into the channel; the projections on the lens engaged within the slots in the brow member to lock the lens within the channel; and two side shield members, said side shield members attached to corresponding temple arm members, the side shields each including a projecting nub extending into the temple arm, the nub including a central opening, and the temple arm surrounding the nub and filling the opening to secure the side shield to the corresponding temple arm.

8. Eyewear comprising: a brow member; two temple arm members, each temple arm member pivotally attached to opposite ends of the brow member; a lens attached to the brow member; and two side shield members, each one of said side shield members attached to one of the temple arm members, the side shields including at least one projecting nub extending into the temple arm, the side shield nub including a central opening, the temple arm member surrounding the nub and engaging the side shield within the central opening.

9. Eyewear as claimed in claim 8 wherein the lens member is removably attached to the brow member.

10. Eyewear as claimed in claim 9 wherein the attachment of the brow member with the lens member is made within a channel formed within the brow member.

11. Eyewear as claimed in claim 10 wherein the lens member includes a series of projections along one edge thereof, the brow member having a corresponding series of slots opening into the channel, and the projections on the lens engaging within the slots in the brow member to lock the lens within the brow channel.

12. Eyewear comprising: a brow member having a channel; two temple arm members, each temple arm member pivotally attached to opposite ends of the brow member; a lens member includes a series of projections along one edge thereof, the brow member having a corresponding series of slots opening into the channel, and the projections on the lens removably engaged within the slots in the brow member to lock the lens within the brow channel, a groove having a curve edge surrounding the projections within the lens; and two side shield members, each one of said side shield members attached to one of the temple arm members, the side shields including at least one projecting nub extending into the temple arm, the temple arm surrounding the nub to lock the side shield to the temple arm.

13. Eyewear, comprising:
   a brow member;
   two temple arm members, each temple arm pivotally attached to opposite ends of the brow member;
   a lens, removably attached to the brow member within a channel formed in the brow member;
   the lens having a series of slots adjacent one edge thereof; and
   the brow member having a corresponding series of brow slots opening into the channel and a series of projections extending into the channel opposite the brow slots,
   the lens engaged within the channel with the projections engaging the slots in the lens to lock the lens within the channel.

14. Eyewear as claimed in claim 13 wherein the brow slots are formed in the front surface of the brow member and the projections extend into the channel in the brow member from the rear surface thereof.

15. Eyewear as claimed in claim 14 wherein the projections include a substantially triangular cross-section perpendicular to the plane portion, the triangular cross-section having a base integral with the brow member and an apex for projection into the openings in the channel.

16. Eyewear as claimed in claim 13 further comprising two side shield members, each one of said side shield members attached to one of the temple arm members.

17. Eyewear as claimed in claim 16 wherein the side shields each include at least one projecting nub extending into the temple arm, the temple arm surrounding the nub to lock the side shield to the temple arm.

18. Eyewear as claimed in claim 17 wherein the nub includes a central opening and the temple arm fills the opening to lock the side shield to the temple arm.

19. Eyewear as claimed in claim 13 wherein the lens is made of a polycarbonate material and the brow member and temple arm members are made of a flexible plastic material.

* * * * *